(12) United States Patent
Destaillats et al.

(10) Patent No.: US 11,278,047 B2
(45) Date of Patent: Mar. 22, 2022

(54) LIPID COMPOSITION FOR USE IN INFANTS AND YOUNG CHILDREN FOR PROMOTING GUT COMFORT AND OPTIMAL FAT AND CALCIUM ABSORPTION

(71) Applicant: NESTEC S.A., Vevey (CH)

(72) Inventors: Frederic Destaillats, Servion (CH); Valerie Petit, Thonon-les-Bains (FR)

(73) Assignee: Societe des Produits Nestle S.A., Vevey (CH)

( * ) Notice: Subject to any disclaimer, the term of this patent is extended or adjusted under 35 U.S.C. 154(b) by 200 days.

(21) Appl. No.: 16/321,559

(22) PCT Filed: Jul. 28, 2017

(86) PCT No.: PCT/EP2017/069155
§ 371 (c)(1),
(2) Date: Jan. 29, 2019

(87) PCT Pub. No.: WO2018/024629
PCT Pub. Date: Feb. 8, 2018

(65) Prior Publication Data
US 2019/0166898 A1 Jun. 6, 2019

(30) Foreign Application Priority Data

Aug. 5, 2016 (EP) .................................. 16183006

(51) Int. Cl.
*A23L 33/00* (2016.01)
*A23L 33/12* (2016.01)
(Continued)

(52) U.S. Cl.
CPC .............. *A23L 33/40* (2016.08); *A23L 33/12* (2016.08); *A61K 31/20* (2013.01); *A61K 31/702* (2013.01);
(Continued)

(58) Field of Classification Search
CPC .......... A23V 2250/206; A23V 2002/00; A23V 2250/54246; A61K 31/702
See application file for complete search history.

(56) References Cited

U.S. PATENT DOCUMENTS 5,601,860 A * 2/1997 Lien ........................ C11C 3/10
426/72
2003/0026860 A1 2/2003 Lasekan et al.
2011/0244071 A1 10/2011 Bar-Yoseph et al.

FOREIGN PATENT DOCUMENTS

EP 1237419 12/2012
WO 2007090894 8/2007
(Continued)

OTHER PUBLICATIONS

Perales et al. "Bioavailability of Calcium from Milk-Based Formulas and Fruit Juices Containing Milk and Cereals Estimated by in Vitro Methods (Solubility, Dialyzability, and Uptake and Transport by Caco-2 Cells)" Journal of Agricultural and Food Chemistry, 2005, vol. 53, pp. 3721-3726.
(Continued)

*Primary Examiner* — Erik Kashnikow
*Assistant Examiner* — Assaf Zilbering
(74) *Attorney, Agent, or Firm* — K&L Gates LLP

(57) ABSTRACT

The present invention relates to a nutritional composition, for infants and young children (about 12 to 36 months) in which the sum of the triacylglycerols (TAG) sn-1(3) palmitic acid (PA), myristic acid (MA) and stearic acid (SA) constitutes less than 13.0% of the TAG. The composition promotes absorption of fatty acids and calcium in the gut, improves gut comfort, decreases abdominal pain associated with hard stool formation, promotes regular bowel movements and reduces the incidence and severity of constipation in infants and young children (up to the age of about three
(Continued)

Control formula
sn-1,3 LCSFA= 24.7% of TAG

Formula- Blend 2
sn-1,3 LCSFA= 8.9% of TAG

Formula –Blend 3
sn-1,3 LCSFA= 11.2% of TAG

▨ Insoluble calcium   ▢ Soluble calcium years old). The composition also promotes bone mineralization, increasing bone strength and bone mineral density.

9 Claims, 1 Drawing Sheet

(51) Int. Cl.
  *A61K 31/702* (2006.01)
  *A61K 31/20* (2006.01)
(52) U.S. Cl.
  CPC ... *A23V 2002/00* (2013.01); *A23V 2250/1886* (2013.01); *A23V 2250/206* (2013.01); *A23V 2250/502* (2013.01); *A23V 2250/54246* (2013.01); *A23V 2250/54252* (2013.01); *A23V 2250/55* (2013.01); *A23V 2250/612* (2013.01); *Y02A 50/30* (2018.01)

(56) References Cited

FOREIGN PATENT DOCUMENTS

| WO | 2013068879 | 5/2013 |
|----|-----------|--------|
| WO | 2016050754 | 4/2016 |

OTHER PUBLICATIONS

Nagy et al. "Mapping the regiosomeric distribution of fatty acids in triacylglycerols by hybrid mass spectrometry" Journal of Lipid Research, 2013, vol. 54, pp. 290-305.

Bar-Yoseph et al. "SN2-Palmitate Reduces Fatty Acid Excretion in Chinese Formula-fed Infants" JPGN, 2016, vol. 62, No. 2, pp. 341-347.

Beggio et al. "Robotized method for the quantification of fatty acids by gas-liquid chromatography" Eur. J. Lipid Sci. Technol., 2013, vol. 115, pp. 825-830.

Carnielli et al. "Structural Position and Amount of Palmitic Acid in Infant Formulas: Effects on Fat, Fatty Acid, and Mineral Balance" Journal of Pediatric Gastroenterology and Nutrition, 1996, vol. 23, pp. 553-560.

Lopez-Lopez et al. "The influence of dietary palmitic acid triacylglyceride position on the fatty acid, calcium and magnesium contents of at term newborn faeces" Early Human Development, 2001, vol. 65, pp. S83-S94.

Nowacki et al. "Stool fatty acid soaps, stool consistency and gastrointestinal tolerance in term infants fed infant formulas containing high sn-2 palmitate with or without oligofructose: a double-blind, randomized clinical trial" Nutrition Journal, 2014, vol. 13, No. 105, 11 pages.

Patent Abstract—Zhang-Bin et al. "Effects of infant formula containing palm oil on the nutrient absorption and defecation in infants: a meta-analysis" 2 pages, XP002762425.

\* cited by examiner

Control formula
sn-1,3 LCSFA= 24.7% of TAG
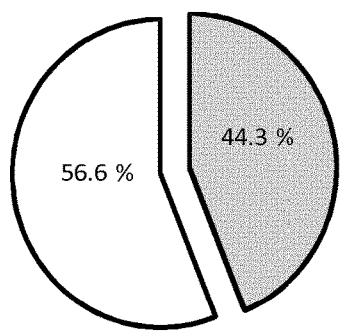
Formula- Blend 2
sn-1,3 LCSFA= 8.9% of TAG
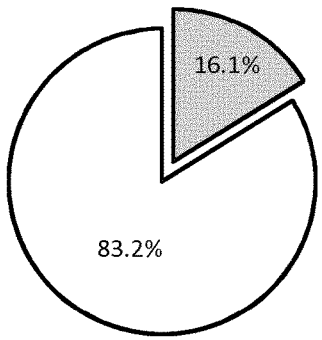
Formula –Blend 3
sn-1,3 LCSFA= 11.2% of TAG
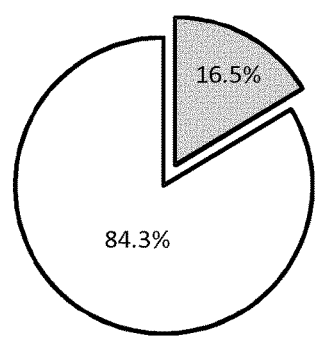
▨ Insoluble calcium   ▢ Soluble calcium

LIPID COMPOSITION FOR USE IN INFANTS AND YOUNG CHILDREN FOR PROMOTING GUT COMFORT AND OPTIMAL FAT AND CALCIUM ABSORPTION

CROSS REFERENCE TO RELATED APPLICATIONS

The present application is a National Stage of International Application No. PCT/EP2017/069155, filed on Jul. 28, 2017, which claims priority to European Application No. 16183006.2, filed on Aug. 5, 2016, the entire contents of which are being incorporated herein by reference.

TECHNICAL FIELD

The present invention relates to a nutritional composition, for infants and young children (about 12 to 36 months) in which the sum of the triacylglycerols (TAG) sn-1(3) palmitic acid (PA), myristic acid (MA) and stearic acid (SA) constitutes less than 13% of the TAGs. The composition consistently promotes absorption of fat and calcium in the gut, improves gut comfort, decreases abdominal pain associated with hard stool formation, promotes regular bowel movements and reduces the incidence and severity of constipation.

BACKGROUND OF THE INVENTION

Breast feeding is considered as the ideal source of nutrition and is the preferred choice for feeding infants up to at least 6 months of age. Consequently, human milk (HM) has long been considered as the model for the design of infant formulas (IF). Even many improvements in the nutrient composition of IF have been made during the last decades, there are still important differences in composition as well as in functional benefits conveyed by HM. In particular, differences are still observed in fat and calcium absorption as well as in gastrointestinal tolerance between breast-fed (BF) and formula-fed (FF) infants. FF infants have lower absorption of both fat and Ca than BF infants. Furthermore, BF babies have frequent, watery or loose soft stools whereas FF infants have less frequent bowel movements, firmer stools that may be difficult to pass and therefore, may lead to discomfort with pain, and in some cases, constipation. These abnormalities or particularities in stooling patterns are perceived as abnormal by parents and thus a common source of parental distress and a frequency cause of consultation to health care provider.

The differences in the occurrence of digestive disorders in BF and FF infants can be attributed to the different lipid composition of BM compared to that of IF, in particular, the differences in triglyceride (triacylglycerol, TAG) composition.

More than 98% of human milk fat is in the form of TAG that contains saturated and unsaturated fatty acids (FA) esterified at the sn-1, -2 and -3 positions of a sn-glycerol molecule. Human milk is rich in the saturated fatty acids (SFA), palmitic acid (PA) (representing ~20-25% of total FA) of which over 50 to 70% is esterified in sn-2 position of the glycerol backbone. This configuration is accompanied by positioning of the unsaturated FA oleic and linoleic acids at the sn-1(3) position of the TAG. Cow's milk, like HM, contains high amount of PA (about 23-32.3% of total FA) but about only 45% of PA is esterified in the sn-2 position of the TAG, with 47% PA at sn-1 position and 7.5% at sn-3 position. Vegetable oils like palm oil, used in IF, while having a similar level of overall PA compared to BM, have a high percentage, typically 80-85% or more of palmitic acid present in the TAG sn-1 or sn-3 position.

Palmitic acid (and other fatty acids) esters, in the sn-1 and sn-3 TAG position are most likely to be cleaved during digestion and form free fatty acids. Free palmitic acid can bind calcium and form insoluble palmitic acid soaps in the intestine. Excretion of these soaps in the feces may be partially responsible for harder stools experienced by some FF infants.

Moreover, as a result of these abnormalities in stool patterns and in fat and calcium absorption, infants who are fed conventional IF may also suffer from undernourishment (impaired growth), digestive disorders, for example, colic, reduced appetite and regurgitation and even intolerances to food components. Digestive disorders, including colic may manifest as diarrhea, excessive gas, and abdominal discomfort and pain that may cause excessive crying and fussiness in the infant or young child.

Hard stools may lead to constipation, fussiness and crying, poor feeding tolerance, digestive discomfort, and abdominal pain. Stools tend to become harder with age. This may be related to dietary changes or changes in gut motility. For example, as the BF infant begins to digest food other than breast milk, especially other protein sources, the incidence of constipation increases. Similarly, when the FF infant starts to consume protein sources other than milk, the incidence of constipation may increase. As tendency for harder stools increases with age, young children may be more prone to constipation than infants.

Thus, according to one embodiment of the invention, the compositions of the invention reduces the incidence and severity of constipation in infants and young children.

The formation of insoluble fatty acid soaps in the intestine also leads to poor fat and calcium bioavailability.

Further, calcium loss in a population such as infants may increase the risk of insufficient bone mineralization.

Poor fat absorption may lead to undernourishment and poor thriving, as fat is a compact source of energy (providing 40-50% of calorie requirements)

To improve fat and calcium bioavailability in FF infants, IFs have been developed with relatively low total PA levels so that the amount of sn-1(3) PA in the fat blend does not exceed the amount of sn-1(3) PA in human milk fat. Also, the proportion of PA in the sn-2 position has been increased by using structured TAGs, hence reducing the sn-1(3) PA amounts. It is known that decreasing PA amounts in the sn-1(3) by using structured TAGs improves PA absorption through reduction of stool palmitic acid soap formation when compared to vegetable oil based-formula rich in sn-1(3) palmitic acid.

However, studies have failed to consistently demonstrate benefits for stool softening and for fat and Ca absorption.

For example, Carnielli et al. [Structural position and amount of palmitic acid in infant formulas: effects on fat, fatty acid, and mineral balance. J. Pediatr. Gastroenterol. Nutr. 1996 December; 23(5):553-60] showed that infants who consumed structured TAG formula containing 8.5% of total FAs as sn-1(3) PA had better PA absorption than infants fed conventional IF with 18.2% of total FAs as sn-1(3) PA. Interestingly, reduction of sn-1(3) PA was associated with better absorption of saturated FAs (i.e. lauric, myristic, palmitic, stearic acids) besides palmitic acid. No significant differences were observed for mono- and polyunsaturated FAs. These results are coherent with those of other studies where stools of infants fed IF containing structured TAGs with 10.1% to 14.6% of total FAs as sn-1(3) PA had significantly lower saturated FA content mostly excreted as soaps than infants fed conventional formula. It remains unclear how palmitic acid soaps may act on the absorption of the other saturated FAs [Lopez-Lopez A, et al. The influence of dietary palmitic acid triacylglyceride position on the fatty acid, calcium and magnesium contents of at term newborn faeces. Early Hum Dev 2001 November; 65 Suppl: 583-594, and Bar-Yoseph et al., SN2-Palmitate Reduces Fatty Acid Excretion in Chinese Formula-fed Infants. J Pediatr Gastroenterol Nutr 2016 February; 62(2):341-7.].

In patent EP1237419B2 from Nutricia, IF compositions are provided in which the lipid component comprises fatty acid TAG in which PA residues make up more than 10%, preferably 16 to 24% of all FA esters present in the TAG and in which at least 30% of the triglycerides are in the sn-2 position. The IFs of EP 123 7419 also include a prebiotic, which are known to soften stools. Pre- and probiotics are known to encourage the growth of a healthy microbiota in infants and young children so that their intestinal flora resembles more closely that of breastfed children. The compositions of EP1237419 also contain hydrolyzed protein. Hydrolyzed protein improves digestibility, in particular, with respect to reducing the risk of an allergic response to cow's milk proteins.

WO2013/068879 describes IF compositions used to improve stool consistency. The IFs contain oligofructose (at least 0.45 g/100 kcal) to increase the bifidobacteria amount in the colon and 7.5%-12% of the lipid component consists of 7.5%-12% PA in the sn-2 position (to reduce calcium soaps).

There is a need for nutritional compositions for use in formulas for infants or young children to improve stool consistency and to reduce calcium excretion in stools (in the form of soaps), specifically so that the stooling pattern and Ca and lipid absorption is closer to that observed in infants fed with human milk.

There is a need for nutritional compositions for use in formulas for infants or young children that are nutritionally balanced (in terms of fatty acids) and that can improve digestive comfort and decrease or eliminate abdominal pain in infants and young children.

There is a need for nutritional compositions for use in formulas for infants or young children that facilitates regular bowel movements, prevents or reduces the incidence and/or severity of constipation in infants or young children.

There is a need to provide nutritional compositions that promote absorption of both fat and calcium in infants or young children.

There is a need to provide nutritional compositions to increase bone mineralization, increase bone strength, and/or increase bone mineral density in infants or young children.

There is a need to provide nutritional compositions to ensure healthy growth in infants or young children.

Up until now, the influence of other sn-1(3) long-chain saturated fatty acids (LC-SFA) other than PA, namely myristic (14:0) and stearic (18:0) acids, have not been considered important contributors to reduced availability of fat and Ca, and stool hardness in FF infants. The applicant, in a series of studies, has determined that the sum (total amount) of these three sn-1(3) LC-SFA (i.e. myristic, palmitic and stearic acids) in the TAG is important in favoring fatty acid and calcium (Ca) absorption and in producing stool patterns closer to that of BF infants.

The applicant has defined TAG profiles for the lipid component of nutritional compositions that are advantageous in reducing digestive discomfort and/or reducing abdominal pain and/or reducing the risk of constipation in infants and/or young children.

The applicant has thus determined that nutritional compositions having a sum of sn-1(3) myristic, palmitic and stearic acids generally less than 13% (w/w) of TAG may improve gastrointestinal tolerance, fat and Ca bioavailability in infants and young children. Specifically, they have determined that the sum of sn-1(3) MA, PA and SA less than 13% of TAG consistently favors fat and Ca absorption by decreasing fatty acid calcium soap formation. They have also determined that the nutritional compositions comprising lipids in which the sum of sn-1(3) MA, PA and SA of less than 13% of TAG consistently improves stool consistency and produces stool patterns closer to that of BF infants.

Results from in vitro digestion studies by the applicant demonstrate the efficacy of the compositions with lipids having the above defined limited amounts of sn-1(3) PA, SA and MA.

SUMMARY OF THE INVENTION

In a first aspect the invention relates to a composition for infants or young children comprising protein, carbohydrates and lipids, said lipids comprising fatty acid (FA) triacylglycerols (TAG), said fatty acid TAG comprising stearic, palmitic and myristic esters, wherein the sum of the amount of stearic, palmitic and myristic esters at the sn-1(3) position of the TAG is less than 13.0% (w/w) of TAG and the myristic acid represents up to 3.6% of the total FA, the palmitic acid represents up to 11.1% of the total FA and stearic acid represents up to 4.6% of the total FA (w/w).

In an embodiment of the invention the sum of the total palmitic, and myristic, and stearic esters of the TAG is less than 19.3% (w/w) of total fatty acid TAG.

In an embodiment of the invention the carbohydrates of the composition consist of 99% to 100% of lactose.

In an embodiment of the invention the amount of protein in the composition is less than or equal to 3.0 or 2.1 g protein/100 kcal of composition, preferably less than or equal to 1.9 g protein/100 kcal, more preferably, less than or equal to 1.8 g protein/100 kcal and most preferably less than or equal to 1.7 g protein/100 kcal.

In an embodiment of the invention protein is a mixture of whey protein and casein wherein the ratio of whey protein to casein is between 50:50 and 80:20.

In an embodiment of the invention the protein is partially hydrolyzed.

In an embodiment of the invention the composition also comprises at least one prebiotic, preferably selected from 2'Fucosyllactose, Lacto-difucotetraose, 3-Fucosyllactose, Lacto-N-fucopentaose I, Lacto-N-fucopentaose II, Lacto-N-fucopentaose III, Lacto-N-neotetraose, Lacto-N-tetraose, 3'Sialyllactose, 6'Sialyllactose, 3'Sialyllacto-N-tetraose, 6'Sialyl-Lacto-N-neotetraose, inulin, fructooligosaccharide (FOS), short-chain fructooligosaccharide (short chain FOS), galacto-oligosaccharide (GOS), xylooligosaccharide (XOS), ganglioside, partially hydrolyzed guar gum, acacia gum, soybean-gum, or mixtures thereof.

In an embodiment of the invention the composition also comprises probiotics, preferably selected from *Lactobacillus paracasei, Lactobacillus rhamnosus, Bifidobacterium longum, Bifidobacterium lactis*, and *Bifidobacterium breve, Bifidobacterium animalis, Bifidobacterium infantis, Bifidobacterium adolescentis, Lactobacillus acidophilus, Lactobacillus casei, Lactobacillus salivarius, Lactobacillus lactis, Lactobacillus reuteri, Lactobacillus johnsonii, Lactobacillus plantarum, Lactococcus lactis, Streptococcus thermo-*

*philus, Enterococcusfaecium, Saccharomyces cerevisiae, Saccharomyces boulardii*, and *E. Coli* Nissle. In particular, probiotics and non-replicating probiotics, such as the genus *Lactobacillium, Bifidobacterium* or combination thereof, for example *Lactobacillus johnsonii, Lactobacillus paracasei, Lactobacillus rhamnosus, Bifidobacterium longum, Bifidobacterium lactis, Bifidobacterium breve*, or combinations thereof, and/or non-viable fractions of these bacteria.

In an embodiment of the invention the lipids of the composition comprise DHA and/or ARA and/or EPA.

In an embodiment of the invention the composition is used in reducing digestive discomfort and/or reducing abdominal pain and/or reducing the incidence and/or severity of colic and/or reducing the incidence and/or severity of constipation in infants or young children.

Said reduction in digestive discomfort and/or abdominal pain and/or reduction in the incidence and severity of colic and/or reduction of the incidence and/or severity of constipation may comprise reducing the stool hardness, preferably to render the stool consistency close to that of breast fed infants or young children with a normal stool pattern.

In an embodiment of the invention the composition is used for improving calcium homeostasis and calcium and lipid absorption, increasing calcium and lipid retention, and/or in reducing the formation of palmitic acid or stearic acid or myristic acid soaps in infants or young children.

In an embodiment of the invention the composition is used for increasing bone mineralization, increasing bone strength, and/or increasing bone mineral density in infants or young children.

DESCRIPTION OF THE DRAWINGS

FIG. 1: reports results of in vitro calcium solubility from digested infant formula samples containing different amount of sn-1,3 LCSFA (Example 4).

DETAILED DESCRIPTION

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to.

Unless defined otherwise, all technical and scientific terms used herein have the same meaning as commonly understood by one of ordinary skill in the art.

The term "infant" will in the context of the present invention mean a child under the age of 12 months.

The term "young child" or "young children" refers to a child in the age from 12 months to 3 years.

In the context of the present invention, the infant may be any term infant or preterm infant. In an embodiment of the invention, the infant is selected from the group of preterm infants and term infants.

The term "infant formula" (or "IF") as used in the context of the present invention refers to a nutritional composition intended for infants during the first months of life and as defined in Codex Alimentarius, (Codex STAN 72-1981) and Infant Specialities (incl. Food for Special Medical purposes) as defined in Codex Alimentarius, (Codex STAN 72-1981). The term "follow-on formula" is given to formulas designed to be used from the age of 6 to 12 months of age.

The term "growing-up milk" is given to formulas designed to be used from the age of one year onwards, generally, until three years of age. It is generally a milk-based beverage adapted for the specific nutritional needs of young children.

A "fortifier" may be defined as a composition for either premature infants and/or term infants who are "small for gestational age" infants, who require additional nutrients to support their growth.

The term "composition for use in formulas for infants or young children" refers in the context of the present invention to either a formula as such, i.e., an infant formula (IF), which comprises all nutrients necessary in order to meet the standards of being an infant formula as defined in the Codex Alimentarius. Further, the "composition for use in formulas for infants or young children" may be a composition comprising nutrients, which, together with other nutrients, can be mixed to prepare a formula, i.e. such "composition for use in infant formulation" can be added to a mixture, which is intended to be used as an infant formula. Further, the "composition for use in formulas" can be a supplement or a fortifier to an infant formula, follow-on formula, growing-up milk or human milk.

Palmitic Acid (PA), Myristic Acid (MA) and Stearic Acid (SA):

In the context of the present invention, the term "palmitic acid" (PA) refers to the saturated fatty acid, 16:0. The term "palmitate" or "palmitic acid ester" may also be used for "palmitic acid" when esterified to glycerol such as in triacylglycerols (TAG). The following terms are used to describe the PA regiospecific distribution in TAG. When PA is esterified in the (external) alpha, first or third position of a TAG, the PA is in the sn-1 or sn-3 position of the TAG. Such PA is in the context of the present invention referred to as sn-1(3) palmitate or sn-1(3) PA or sn-1(3) PA ester or sn-1(3) palmitic acid or sn-1(3) palmitic acid ester. PA esterified in the internal (or beta) position known as the sn-2 position or beta of a TAG is, in the context of the present invention, referred to as sn-2 palmitate, or sn-2 PA or sn-2 PA ester or sn-2 palmitic acid or sn-2 palmitic acid ester. The nutritional compositions of the present invention comprise a lipid component, comprising TAG.

In the context of the present invention, the term "myristic acid" (MA) refers to the saturated fatty acid, 14:0. The term "myristate" or "myristic acid residue" or "MA ester" may also be used for "myristic acid" when esterified in TAG.

When MA is esterified in the (external) alpha, first or third position of a TAG, the PA is in the sn-1 or sn-3 position of the TAG. Such MA is in the context of the present invention referred to as sn-1(3) myristate or sn-1(3) MA or sn-1(3) MA ester or sn-1(3) myristic acid or sn-1(3) myristic acid ester. MA esterified in the internal (or beta) position known as the sn-2 position or beta of a TAG is, in the context of the present invention, referred to as sn-2 myristate, or sn-2 MA or sn-2 MA ester or sn-2 myristic acid or sn-2 myristic acid ester.

In the context of the present invention, the term "stearic acid" (SA) refers to the saturated fatty acid, 18:0. The term "stearate" or "stearic acid ester" may also be used for "stearic acid" when esterified in TAG.

When SA is esterified in the (external) alpha, first or third position of a TAG, the SA is in the sn-1 or sn-3 position of the TAG. Such SA is in the context of the present invention referred to as sn-1(3) stearate or sn-1(3) SA or sn-1(3) SA ester or sn-1(3) stearic acid or sn-1(3) stearic acid ester. SA esterified in the internal (or beta) position known as the sn-2 position or beta of a TAG is, in the context of the present invention, referred to as sn-2 stearate, or sn-2 SA or sn-2 SA ester or sn-2 stearic acid or sn-2 stearic acid ester.

In the context of the present invention percentages (%) are exposed as weight per weight (w/w) value.

In the context of the present invention, the term "sum of the palmitic acid and stearic acid and myristic acid esters positioned in the sn-1(3) position of the TAG" or "sn-1(3) LCSFA" refers to the amount of sn-1(3) palmitic acid plus the amount of sn-1(3) myristic acid plus the amount of sn-1(3) stearic acid, based on amount of palmitic acid plus myristic acid plus stearic acid present in the form of TAG.

Similarly, the term "amount sn-1(3) palmitic acid" refers to the amount of alpha palmitic acid, based on total amount palmitic acid in the TAG.

The invention concerns nutritional compositions and uses thereof in nutritional compositions for infants and young children. The nutritional compositions comprise protein, carbohydrates and lipids.

The applicant has carried out a study based on a set of published clinical trials reporting fat and Ca absorption and/or stool consistency in infants. The applicant has analysed the TAG composition and regiospecific distribution in the oil TAG mixtures of the IFs used in the trials to determine an advantageous FA composition and TAG profile (i.e., regiospecific distribution of FA on TAG).

This study was performed by using a database containing the composition of FA and their distribution on TAG of 450 commercially available fats and oils. FA composition and the corresponding TAG regiospecific distribution in these fats and oils were performed by gas-chromatography [Beggio M, Giuffrida F, Golay P, Nagy K, Destaillats F. Robotized method for the quantification of fatty acids by gas-liquid chromatography. Eur J Lipid Sci Technol 2013; 115:825-30] and by non-aqueous reversed phase liquid chromatography and hybrid mass spectrometry [Nagy K, Sandoz L, Destaillats F, Schafer O. Mapping the regioisomeric distribution of fatty acids in triacylglycerols by hybrid mass spectrometry. J Lipid Res 2013 January; 54(1):290-305], respectively. The FA composition and the FA regiospecific distribution in positions sn-1 (3) and sn-2 of each type of oils in the database was the mean composition of 1 to 21 individual samples from different world-wide locations. The sum of LC-SFA in sn-1(3) position of TAG for each oils and fats was calculated. The results are reported in Tables 1 and 2 below.

TABLE 1

Myristic, palmitic and steric acids content in various vegetable oils and milk fat

|  | Corn oil (n = 13) | | Soy oil (n = 21) | | Palm olein (n = 18) | | Kernel oil (n = 3) | | Palm oil (n = 14) | |
| --- | --- | --- | --- | --- | --- | --- | --- | --- | --- | --- |
|  | Mean g/100 g fat | SD | Mean g/100 g fat | SD | Mean g/100 g fat | SD | Mean g/100 g fat | SD | Mean g/100 g fat | SD |
| Myristic acid (14:0) | 0.0 | 0.0 | 0.1 | 0.0 | 0.9 | 0.1 | 14.4 | 0.2 | 1.0 | 0.1 |
| Palmitic acid (16:0) | 11.1 | 0.7 | 9.9 | 0.4 | 36.3 | 2.0 | 7.6 | 0.2 | 40.2 | 1.7 |
| Stearic acid (18:0) | 2.0 | 0.6 | 3.7 | 0.4 | 3.9 | 0.3 | 2.0 | 0.0 | 4.2 | 0.2 |
| Saturated fatty acids - All | 13.9 | 0.6 | 14.4 | 0.6 | 42.0 | 2.2 | 75.1 | 0.7 | 46.4 | 1.6 |
| Monounsaturated fatty acids (MUFA) | 29.2 | 3.3 | 22.4 | 1.7 | 40.4 | 1.4 | 14.3 | 0.1 | 37.6 | 0.3 |
| Polyunsaturated fatty acids (PUFA) | 48.8 | 3.2 | 55.6 | 1.8 | 10.6 | 0.9 | 2.3 | 0.1 | 9.3 | 0.5 |
| Omega-3 fatty acids (n-3) | 1.0 | 1.0 | 6.1 | 0.7 | 0.2 | 0.0 | 0.0 | 0.0 | 0.1 | 0.1 |
| Omega-6 fatty acids (n-6) | 47.8 | 2.9 | 49.5 | 1.2 | 10.5 | 0.9 | 2.3 | 0.1 | 9.1 | 0.4 |

|  | Coconut oil (n = 8) | | Sunflower oil (n = 10) | | High oleic sunflower oil (n = 10) | | Rapeseed oil (n = 13) | | High oleic safflower oil (n = 1) | Milk fat (n = 11) | |
| --- | --- | --- | --- | --- | --- | --- | --- | --- | --- | --- | --- |
|  | Mean g/100 g fat | SD | Mean g/100 g fat | SD | Mean g/100 g fat | SD | Mean g/100 g fat | SD | g/100 g fat | Mean g/100 g fat | SD |
| Myristic acid (14:0) | 16.5 | 0.5 | 0.1 | 0.0 | 0.0 | 0.0 | 0.1 | 0.0 | 0.1 | 9.8 | 0.6 |
| Palmitic acid (16:0) | 8.5 | 0.3 | 5.9 | 0.5 | 3.7 | 0.6 | 4.5 | 1.3 | 4.8 | 26.6 | 1.9 |
| Stearic acid (18:0) | 2.6 | 0.3 | 3.1 | 0.3 | 2.8 | 0.2 | 1.7 | 0.3 | 1.9 | 8.8 | 0.8 |
| SFA- All | 84.1 | 1.3 | 10.0 | 0.7 | 7.8 | 0.7 | 7.2 | 1.5 | 7.7 | 59.5 | 1.8 |
| MUFA | 6.3 | 0.3 | 30.4 | 7.4 | 75.8 | 3.0 | 59.0 | 2.1 | 75.8 | 18.5 | 1.5 |
| PUFA | 1.5 | 0.1 | 53.7 | 7.3 | 10.0 | 2.7 | 26.2 | 1.3 | 13.1 | 2.2 | 0.5 |
| Ω-3 fatty acids (n-3) | 0.0 | 0.0 | 0.1 | 0.1 | 0.1 | 0.1 | 7.4 | 0.9 | 0.1 | 0.5 | 0.2 |
| Ω-6 fatty acids (n-6) | 1.5 | 0.1 | 53.6 | 7.3 | 9.9 | 2.7 | 18.8 | 1.4 | 13.0 | 1.7 | 0.6 |

TABLE 2

Regiospecific distribution of myristic acid, palmitic acid and stearic acid in various vegetable oils and milk fat

|  | Corn oil (n = 5) | | Soy oil (n = 2) | | Palm olein (n = 15) | | Kernel oil (n = 3) | | Palm oil (n = 14) | |
| --- | --- | --- | --- | --- | --- | --- | --- | --- | --- | --- |
|  | Mean g/100 TAG | SD | Mean g/100 TAG | SD | Mean g/100 TAG | SD | Mean g/100 TAG | SD | Mean g/100 TAG | SD |
| sn-1 (3) Myristic acid (14:0) | 0.0 | 0.0 | 0.0 | 0.0 | 0.5 | 0.2 | 9.4 | 0.3 | 0.6 | 0.1 |
| sn-1 (3) Palmitic acid (16:0) | 11.1 | 0.6 | 10.8 | 0.3 | 35.1 | 3.2 | 6.6 | 0.1 | 37.2 | 2.2 |
| sn-1 (3) Stearic acid (18:0) | 1.3 | 0.5 | 2.5 | 0.6 | 3.3 | 0.6 | 1.6 | 0.2 | 3.5 | 0.7 |
| sn-2 Myristic acid (14:0) | 0.0 | 0.0 | 0.0 | 0.0 | 0.1 | 0.0 | 4.8 | 0.7 | 0.1 | 0.0 |

TABLE 2-continued

Regiospecific distribution of myristic acid, palmitic acid and stearic acid in various vegetable oils and milk fat

| | | | | | | | | | | |
|---|---|---|---|---|---|---|---|---|---|---|
| sn-2 Palmitic acid (16:0) | 0.1 | 0.0 | 0.0 | 0.0 | 2.2 | 2.8 | 1.1 | 0.4 | 3.8 | 1.9 |
| sn-2 Stearic acid (18:0) | 0.3 | 0.2 | 0.1 | 0.0 | 0.2 | 0.3 | 0.4 | 0.2 | 0.2 | 0.2 |
| sum sn-1 (3) myristic, palmitic, stearic acids | 12.5 | 0.6 | 13.3 | 0.3 | 39.0 | 3.7 | 17.6 | 0.5 | 41.3 | 2.3 |

| | Coconut oil (n = 8) | | Sunflower oil (n = 3) | | High oleic sunflower oil (n = 2) | | Rapeseed oil (n = 3) | | High oleic safflower oil (n = 1) | Milk fat (n = 9) | |
|---|---|---|---|---|---|---|---|---|---|---|---|
| | Mean g/100 TAG | SD | Mean g/100 TAG | SD | Mean g/100 TAG | SD | Mean g/100 TAG | SD | g/100 g TAG | Mean g/100 TAG | SD |
| sn-1 (3) Myristic acid (14:0) | 11.0 | 0.9 | 0.0 | 0.0 | 0.0 | 0.0 | 0.0 | 0.0 | 0.0 | 4.3 | 0.3 |
| sn-1 (3) Palmitic acid (16:0) | 7.2 | 0.9 | 5.6 | 0.8 | 3.8 | 0.2 | 4.7 | 0.2 | 5.7 | 14.6 | 1.2 |
| sn-1 (3) Stearic acid (18:0) | 2.4 | 0.9 | 2.0 | 0.6 | 2.5 | 0.5 | 0.6 | 0.1 | 1.8 | 6.6 | 0.7 |
| sn-2 Myristic acid (14:0) | 9.0 | 1.4 | 0.0 | 0.0 | 0.0 | 0.0 | 0.0 | 0.0 | 0 | 4.9 | 0.4 |
| sn-2 Palmitic acid (16:0) | 1.8 | 0.9 | 0.6 | 0.9 | 0.0 | 0.0 | 0.0 | 0.0 | 0 | 10.9 | 0.6 |
| sn-2 Stearic add (18:0) | 0.4 | 0.3 | 0.3 | 0.3 | 0.0 | 0.0 | 0.0 | 0.0 | 0 | 3.1 | 0.3 |
| sum sn-1 (3) myristic, palmitic, stearic acids | 20.5 | 1.4 | 7.6 | 1.4 | 6.2 | 0.7 | 5.3 | 0.3 | 7.5 | 25.5 | 1.3 |

In an in vitro digestion model the applicant further investigated the effect of FA composition and the stereospecific distribution of the FA residues on fat and calcium bioavailability. Based on the results of these analyses, the applicant has determined an advantageous range for the sum of MA, PA and SA in sn-1(3) positions of TAGs to be included in compositions for infants and young children, that reduces digestive discomfort and/or pain and/or reduces abdominal pain and/or reduces the risk of constipation in infants and young children.

Lipids:

According to the one aspect of the invention, the lipids in the nutritional composition comprise TAG that comprise stearic acid, palmitic acid and myristic acid esters. The sum of the amount of palmitic acid and myristic acid and stearic acid residues at the sn-1(3) position of the TAG is generally less than 13% (w/w) of TAG. The lipids may comprise other FA. The daily doses of lipids, and all other compounds administered should always comply with the published safety guidelines and regulatory requirements. This is particularly important with respect to the administration to new-born babies, especially those born with low birth weight, very low or extremely low birth weight. The lipid blend thus conforms to the relevant dietary requirements for inclusion in infant formula.

The skilled person may refer to the FA composition and TAG regiospecific structural composition of a number of oils of Tables 1 and 2 to determine the amount of the given oils he may use in the composition. The skilled person knows how to determine the FA content and regiospecific distribution of a lipid source he wishes to use according to standard methods, including those cited above (Beggio et al. and Nagy K., et al.) used by the applicant in establishing the values cited in Tables 1 and 2.

The lipids in the nutritional composition according to certain embodiment of the invention may be in the form of an oil mix, which refers to a mixture of vegetable fats and oils and/or dairy fats and/or animal fats comprising TAG. The TAG contain stearic acid (SA), palmitic acid (PA) and myristic acid (MA) esters. The oil mix may be a mixture of one or more vegetable oils and fats, for example, rapeseed oil, sunflower oil, high oleic sunflower oil, coconut oil, soybean oil, canola oil, safflower oil, high oleic safflower oil, corn oil and long chain polyunsaturated fatty acid (LC-PUFA)-containing oils, such as oils from certain microalgae and fungi including *Mortierella Alpina*, fish oil, milk fat, animal fat and animal fat fractions. The oil mix may also comprise other vegetable oils and fats suitable for infant nutrition.

TABLE 3

Ranges of typical vegetable oils and milk fat suitable for the nutritional compositions according to the invention.

| Lipid composition | Blend 1 per 100 kcal | Blend 2 per 100 kcal | Blend 3 per 100 kcal |
|---|---|---|---|
| Lipid (g) | 4.4-6 | 4.4-6 | 4.4-6 |
| Milk fat* | — | — | 23.9-29.3% |
| Rapeseed oil* | 17.3-21.1% | 16.9-20.7% | 15.8-19.4% |
| Sunflower oil* | 11.5-14.1% | 11.34-13.9% | 8.2-10% |
| High oleic sunflower oil* | 41.9-51.3% | 42.1-51.5% | 39.2-48% |
| Coconut oil* | 18-22% | 17.5-21.5% | — |
| Fish oil* | 0.81-0.99% | 2.1-2.5% | 1.8-2.2% |
| LC-PUFA-containing oil, (e.g., *Mortierella Alpina* oil)* | 0.45-0.55% | | 0.99-1.2% |

*% of weight of total lipid

Table 3 above gives some examples of ranges of different vegetable oils that may be used to constitute the oil mix of the nutritional compositions according to embodiments of the invention. The values are based on the mean values of oil compositions given in Tables 1 and 2. Other vegetable oils and/or dairy fats and/or animal fats may be used as the lipid component of the compositions of the invention, in addition to or instead of the lipid sources cited in Table 3. The sn-1(3) PA, SA and MA content of these other lipid sources should be known. If it is not known it may be determined, according to methods known to the skilled person and described above. The sum of the sn-1(3) PA, SA and MA generally is less than 13% (w/w) of TAG.

In the Table 3, the individual values of each of the oils may vary independently, as long as the sum of sn-1(3)3 PA and MA and SA esters is less than 13% (w/w) of TAG.

According to an embodiment of the invention, the lipids in the nutritional compositions may comprise 17.3 to 21.1%, preferably, 18.0 to 20.0%, for example, 19.2% of rapeseed oil, 11.5 to 14.1%, preferably 12.0 to 13.5%, for example 12.8% of sunflower oil, 41.9 to 51.3%, preferably 43.0 to 48.0%, for example, 46.6% of high oleic sunflower oil, and 18.0 to 22.0% preferably 19.0 to 21.0% for example 20.0% coconut oil.

According to another embodiment of the invention, the lipids in the nutritional compositions may comprise 16.9 to 20.7%, preferably, 17.5 to 19.0%, for example, 18.8% of rapeseed oil, 11.3 to 13.9%, preferably 12.0 to 13.5%, for example 12.6% of sunflower oil, 42.1 to 51.5%, preferably 45.0 to 49.0%, for example, 46.6% of high oleic sunflower oil, and 17.5 to 21.5% preferably 18.0 to 20.0% for example 19.5% coconut oil.

According to another embodiment of the invention, the lipids in the nutritional compositions may comprise 23.9 to 29.3%, preferably 25.0 to 28.0% for example 26.6% of milk fat, 15.8 to 19.4%, preferably, 16.5 to 18.0%, for example, 17.6% of rapeseed oil, 8.2 to 10.0%, preferably 8.8 to 9.5%, for example 9.1% of sunflower oil, 39.2 to 48.0%, preferably 42.0 to 46.0%, for example, 43.6% of high oleic sunflower oil.

With respect to these embodiments or any other embodiments of the invention, LC-PUFA may also be included in the lipid blend for example containing docosahexaenoic (22:6 n-3, DHA) and/or arachidonic acid, (20:4n-6, ARA) and/or eicosapentaenoic acid (20:5n-3, EPA). ARA generally may added in an amount of up to 2.0% of the total fat. DHA generally may added in an amount of up to 1.0% of the total fat. If EPA is included in the fat blend, it generally does not exceed the quantity of DHA.

With respect to the above-mentioned embodiments of the invention, the skilled person understands that the lipids in the nutritional composition preferably do not include an additional source of sn-1(3) TAG. If they do, the amounts of additional sn-1(3) PA, SA or MA TAG are such that the total sum of the sn-1(3) PA, SA or MA TAG in the nutritional composition is less than 13.0% of the TAG.

From preliminary results of an in vitro digestion study (method described in Example 1), the applicant has determined that IFs having lipids with the sum of sn-1(3) MA, PA and SA below 13.0% (w/w) significantly increase Ca and fatty acid bioavailability, compared to IFs with a higher amount of these sn-1(3) LC-SFA. The initial results indicate that after digestion in the in vitro system, significantly more calcium is found in the aqueous phase of the digestion product when IF digested contains the lipid blend according to the invention, compared to a standard infant formula where the sum of sn-1(3) PA and MA and SA residues is more than 13.0% (w/w) of TAG (i.e. 23.6% w/w).

Thus, the amount of calcium soaps formed is decreased relative to that formed with higher amounts of these sn-1(3) SFA. The nutritional compositions comprising lipids in which the sum of sn-1(3) MA, PA and SA is less than 13.0% (w/w) may reduce digestive discomfort and/or pain and/or reduce abdominal pain and/or reduce the risk of constipation in infants or young children.

In an embodiment of the invention, the nutritional composition comprises lipids having PA, SA and MA in the form of TAGs wherein, the sum (total amount) of the sn-1(3) PA, MA and SA residues is less than 13.0% (w/w) of TAGs. These nutritional compositions are particularly effective in reducing stool hardness in infants or young children. In particular, according to an embodiment of the invention, for infants up to about 6 months old, the compositions lead to a stool consistency that is softer and close to that of BF infants. According to an embodiment of the invention, infants, in particular, those greater than 6 months old, as well as young children, have a lower incidence and severity of constipation when they consume compositions according to embodiments of the invention.

One aspect of the invention, therefore, concerns a nutritional composition for infants or young children comprising protein, carbohydrates and lipids, the lipids comprising PA, SA and MA as TAG, the sum of the sn-1(3) PA, MA and SA being less than 13.0% (w/w) of TAG, for use in reducing digestive discomfort and/or pain and/or reducing abdominal pain and/or reducing the risk of constipation in infants or young children. Specifically, said reduction in digestive discomfort and/or pain and/or reduction abdominal pain and/or reducing the risk of constipation in infants or young children comprises reducing the stool hardness, preferably so that the stool consistency is close to that of BF infants or young children with a normal stool pattern. The lipids may comprise vegetable oil(s) and/or animal fat(s) and/or animal milk.

Stool hardness may be measured using parameters that are known to the skilled person. Digestive discomfort and abdominal pain may be measured by measuring for example the intensity and frequency of infant crying and fussiness, measuring appetite loss, abdominal palpation or other standard methods. Young children may be able to communicate levels of digestive discomfort and abdominal pain.

The reduction of risk of constipation may be measured by monitoring the frequency of bowel movements in the infant or young child.

The applicant has demonstrated, in in vitro digestion studies, that calcium bioavailability is increased by administration of infant formulas according to the invention.

Therefore, these nutritional compositions are particularly effective in increasing calcium absorption, bone mineralization, and/or increasing bone mineral density in infants or young children.

In a further aspect, the present invention concerns a nutritional composition for infants or young children comprising protein, carbohydrates and lipids, wherein the lipids comprise PA, SA and MA as TAG, and the sum of the sn-1(3) PA, MA and SA esters is less than 13.0% (w/w) of TAG for use in increasing bone mineralization, increasing bone strength, and/or increasing bone mineral density.

The nutritional compositions according to embodiments of the invention are particularly effective in increasing fatty acid absorption in infants and young children. These fatty acids are MA, SA and PA, but may also include other FA.

In a further aspect, the present invention concerns a nutritional composition for infants or young children comprising protein, carbohydrates and lipids, wherein the lipids comprise PA, SA and MA in the triacylglycerol form, and the sum of the sn-1(3) PA, MA and SA residues is less than 13.0% (w/w) of TAG for use in promoting healthy growth in infants and young children.

LC-PUFA:

One or more essential long chain polyunsaturated fatty acid (LC-PUFA) may be included in the lipid blend of composition. Examples of LC-PUFA that may be added are docosahexaenoic acid (DHA), arachidonic acid (ARA) and EPA. The LC-PUFA may be added at concentrations so that they constitute greater than 0.01% of the total FA present in the composition. LC-PUFA containing oils may thus be present in an amount of about 0.2%-2% of the total lipid amount in the composition.

Proteins:

The nutritional compositions of the invention may contain a protein source in an amount of not more than 4.0, 3.0 or 2.1 g/100 kcal, preferably 1.6 to 3 g/100 kcal, most preferably 1.8 to 2.1 g/100 kcal. In one embodiment the protein source in the nutritional composition is in an amount between 3.0 and 4.0 g/100 kcal, or less than 3.0 g/100 kcal. In one embodiment the protein source in the nutritional composition is in an amount of at least 1.6 g/100 kcal, or at least 1.8 g/100 kcal. Preferably the upper amount is less than 2.1 g/100 kcal. The upper threshold of 2.1 g/100 kilocalories aims to contribute to the desired effect on stool hardness of the nutritional composition through modulation of the gut microbiota. The minimal amount is the amount necessary for providing sufficient proteins to the body for growth and development, for example at least 1.6 g/100 kcal, at least 1.8 g/100 kcal or at least 2 g/100 kcal. The type of protein is not believed to be critical to the present invention, provided that the minimum requirements for essential amino acid content are met and satisfactory growth is ensured. It is preferred that over 50% by weight of the protein source is whey. In one embodiment, the protein content is between 30% and 80% whey proteins. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

In one embodiment of the invention the nutritional composition comprises protein that is a mixture of whey protein and casein wherein the ratio of whey protein to casein is between 50:50 and 80:20, preferably 60:40.

In one embodiment of the invention the nutritional composition comprises protein that is a mixture of whey protein and casein wherein the ratio of whey protein to casein is between 20:80 and 40:60, preferably 35/65.

In one embodiment of the invention the nutritional composition comprises protein that is 100% whey protein. This embodiment is advantageously suitable for proteins that are hydrolyzed.

In general, the proteins may be intact or hydrolyzed or a mixture of intact and hydrolyzed proteins. It may be desirable to supply partially hydrolyzed proteins (degree of hydrolysis between 2 and 20%), for example for infants believed to be at risk of developing cows' milk allergy. If hydrolyzed proteins are used, the hydrolysis process may be carried out as desired and as is known in the art. For example, a whey protein hydrolysate may be prepared by enzymatically hydrolyzing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In a preferred embodiment, probiotics may be included in the nutritional compositions of the invention. Examples of known probiotic compounds are *Bacillus, Bifidobacterium, Lactobacillus, Lactococcus, Enterococcus, Saccharomyces, Kluyveromyces, Candida, Streptococcus*, in particular selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacilluslactis, Lactobacillus reuteri, Lactobacillus rhamnosus, Lactobacillus johnsonii, Lactobacillus plantarum, Lactococcus lactis, Streptococcus thermophilus, Enterococcusfaecium, Saccharomyces cerevisiae, Saccharomyces boulardii, E. Coli Nissle*. In particular, probiotics and non-replicating probiotics, such as the genus *Lactobacillus, Bifidobacterium* or combination thereof, for example *Lactobacillus johnsonii, Lactobacillus paracasei, Lactobacillus rhamnosus, Bifidobacterium longum, Bifidobacterium lactis, Bifidobacterium breve*, or combination thereof, and applications of these bacteria.

Carbohydrates:

Lactose may represent essentially 100% of the carbohydrate content. Other carbohydrates such as saccharose, maltodextrin, and starch may be also added. However, in a preferred embodiment there may be included in the nutritional composition of the invention carbohydrates that preferably act as prebiotics. For example, prebiotics are preferably selected from 2'Fucosyllactose, Lacto-difucotetraose, 3Fucosyllactose, Lacto-N-fucopentaose I, Lacto-N-fucopentaose II, Lacto-N-fucopentaose III, Lacto-N-neotetraose, Lacto-N-tetraose, 3'Sialyllactose, 6'Sialyllactose, 3'Sialyl-lacto-N-tetraose, 6'Sialyl-Lacto-N-neotetraose, inulin, fructooligosaccharides (FOS), short-chain fructooligosaccharide (short chain FOS), galacto-oligosaccharides (GOS), xylooligosaccharides (XOS), gangliosides, partially hydrolyzed guar gum, acacia gum, soybean-gum, carob (locust lean gum) or mixtures thereof.

The carbohydrate or carbohydrates may be present at about 1 g to 20 g or 1% to 80% or 20% to 60% in the daily doses of the composition. Alternatively, the carbohydrates are present at 10% to 80% of the dry composition, for an example, in an amount of 9 to 14 g/100 kcal.

In preferred embodiments, lactose represents more than 90%, more than 95% or, in most preferred embodiments, more than 98% or more than 99% of the carbohydrate present in the composition.

In one embodiment, the nutritional composition comprises a mix of oligosaccharides according to WO2007/090894 (general teaching and specifically Example 1). It may be in particular used in combination with GOS. The base formula may provide an oligosaccharide mixture which comprises 5-70 wt % of at least one N-acetylated oligosaccharide selected from the group comprising GalNAcα1,3Galβ1,4Glc and Galβ1,6GalNAcα1,3Galβ1,4Glc, 20-90 wt % of at least one neutral oligosaccharide selected from the group comprising Galβ1,6Gal, Galβ1,6Galβ1,4Glc Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc and Galβ1,3Galβ1,3Galβ1,4Glc and 5-50 wt % of at least one sialylated oligosaccharide selected from the group comprising NeuAcα2,3Galβ1,4Glc and NeuAcα2,6Galβ1,4Glc.

Other components may be added to a nutritional composition, such as vitamins and minerals If necessary, the composition of the invention may contain emulsifiers and stabilizers such as soy, lecithin, citric acid esters of mono- and di-glycerides, and the like.

The composition may also contain other substances which may have a beneficial effect such as lactoferrin, nucleotides, nucleosides, gangliosides, polyamines and the like.

Forms of the Nutritional Compositions for Infants and Young Children:

According to one embodiment of the invention, the nutritional composition is an infant formula.

The infant formula according to the present invention may be a starter formula for infants from the age of birth to 4 to 6 months and which provide complete nutrition for this age group (both for term and preterm infants). Further, the infant formula may be a follow-on formula for infants between the ages of four to six months and twelve months which are fed to the infants in combination with increasing amounts of the foods, such as infant cereals and puréed fruits, vegetables and other foodstuffs as the process of weaning progresses.

According to one embodiment of the invention, the nutritional composition is a growing up milk.

The infant formula may also comprise all vitamins and minerals understood to be essential in the daily diet in nutritionally significant amounts. Minimum requirements have been established for certain vitamins and minerals. Examples of minerals, vitamins and other nutrients present in the nutritional composition include vitamin A, vitamin B1, vitamin B2, vitamin B6, vitamin E, vitamin K, vitamin C, vitamin D, folic acid, inositol, niacin, biotin, pantothenic acid, choline, calcium, phosphor, iodine, iron, magnesium, copper, zinc, manganese, chloride, potassium, sodium, selenium, chromium, molybdenum, taurine, and L-carnitine. The minerals are usually added in the salt form.

According to another embodiment of the invention, the nutritional composition is a fortifier or supplement to human breast milk or to an infant formula, or the composition is a composition to be used in making up an infant formula.

The nutritional compositions of the invention can be in a fluid (liquid) form. These can be sold ready to consume (without further dilution).

The products of the invention can be in the form of dehydrated powders which are prepared for consumption by reconstitution with water or milk.

Preparation of Nutritional Compositions:

The nutritional compositions according to the present invention may be prepared by any known or otherwise suitable manner. For example, an infant formula may be proposed by blending together a source of protein with a carbohydrate source and a lipid source in appropriate proportions. If used, emulsifiers may be included at this stage. Vitamins and minerals may be added at this stage, but may also be added later to avoid thermal degradation. Water, preferably water which has been subjected to reverse osmosis or deionized water, may then be added and mixed in to form a liquid mixture. The temperature of mixing is preferably room temperature, but may also be higher. The liquid mixture may then be thermally treated to reduce bacterial loads. The mixture may then be homogenized.

If it is desired to produce a powdered composition, the homogenized mixture is dried in a suitable drying apparatus, such as a spray drier or freeze drier and converted into powder.

Processes used in the manufacture of formulae for infants and young children are based on the concept that the products must be nutritionally adequate and microbiologically safe to consume. Thus, steps that eliminate or restrict microbiological growth are central to production processes. The processing technology for each specific formula is proprietary to the manufacturer but, in general, it involves the preservation of an oil-in-water (o/w) emulsion by dehydration in the case of powder products or, sterilization in the case of ready-to-feed or concentrated liquid products. Powdered infant formula may be produced using various processes, such as dry blending dehydrated ingredients to constitute a uniform formula or hydrating and wet-mixing a mixture of macro-ingredients, such as fat, protein and carbohydrate ingredients and then evaporating and spray drying the resultant mixture. A combination of the two processes described above may be used where a base powder is first produced by wet-mixing and spray drying all or some of the macro-ingredients and then dry blending the remaining ingredients, including carbohydrate, minerals and vitamins and other micronutrients, to create a final formula. Liquid formulae are available in a ready-to-feed format or as a concentrated liquid, which requires dilution, normally 1:1, with water. The manufacturing processes used for these products are similar to those used in the manufacture of recombined milk.

If it is desired to produce a liquid infant formula, the homogenized mixture is filled into suitable containers, preferably aseptically. However, the liquid composition may also be retorted in the container, suitable apparatus for carrying out the filling and retorting of this nature is commercially available.

The invention is further described with reference to the following examples. It will be appreciated that the invention as claimed is not intended to be limited in any way by these examples.

Example 1

In Vitro Digestion Assay:

An in vitro digestion assay of infant formulas (IF) measures the bioavailability of the calcium in the formulas. The method is based on the method described in Perales et al, Bioavailability of Calcium from Milk-Based Formulas and Fruit Juices Containing Milk and Cereals Estimated by in Vitro Methods (Solubility, Dialyzability, and Uptake and Transport by Caco-2 Cells) J. Agric. Food Chem. 2005, 53, 3721-3726 3721) with some adaptions.

The assay is a two-step infant digestion model that includes a gastric and intestinal digestion phase in a microenvironment similar to that of young infants. After digestion with pepsin, gastric lipase, pancreatin and bile extract, the solubility/insolubility of calcium in the infant formulas is measured in a solubility assay. In the method used by the applicant, a pH of 5.5 and 6.5 are used for the gastric and intestinal phases, respectively. The following concentrations of enzymes are used: gastric lipase (18 U/ml), pepsin (450 U/ml), pancreatin (30.9 mg/ml) and bile extract (2 mM). No dialysis is carried out.

Centrifugation of the intestinal digests to yield a creamy phase, an aqueous phase and a pellet. The calcium content is assessed in each of these phases. The total calcium content in IF and the soluble calcium (found in the aqueous and creamy phase) are determined. From this data the calcium solubility/insolubility of infant formulas is determined The results indicate that the amount of calcium in the pellet (i.e., calcium in the form of an insoluble soap) was significantly lower in formulas containing lower amounts of sn-1(3) saturated fatty acids PA, MA and SA, compared to formulas with higher amounts of sn-1(3) PA, MA and SA. The studies demonstrate that in digestion of IFs containing sn-1(3) PA, MA and SA within the prescribed ranges according to the present invention, less calcium precipitated as soap and thus, more calcium was soluble and available to be absorbed, compared to standard infant formulas containing higher amounts of sn-1(3) PA, MA and SA.

The reference composition of the standard IF is given below:

TABLE 1

Vegetable oil composition of a standard IF

| Lipid mixture composition | Standard IF per 100 kcal |
| --- | --- |
| Lipid (g) | 4.4-6.0 |
| Palm olein* | 47.9% |

TABLE 1-continued

Vegetable oil composition of a standard IF

| Lipid mixture composition | Standard IF per 100 kcal |
|---|---|
| Rapeseed oil* | 20.0% |
| Coconut oil* | 19.9% |
| Sunflower oil* | 10.7% |
| Fish oil* | 1.0% |
| LC-PUFA-containing oil, (e.g., *Mortierella Alpina* oil)* | 0.5% |

*% of weight of total lipid

Example 2: Fat Blends in Nutritional Compositions for Infants and Young Children

TABLE 1

Three examples of lipid blends illustrating the invention

| Fat mixture composition | Blend 1 per 100 kcal | Blend 2 per 100 kcal | Blend 3 per 100 kcal |
|---|---|---|---|
| Lipid (g) | 4.4-6 | 4.4-6 | 4.4-6 |
| Milk fat* | — | — | 26.6% |
| Rapeseed oil* | 19.2% | 18.8% | 17.6% |
| Sunflower oil* | 12.8% | 12.6% | 9.1% |
| High oleic sunflower oil* | 46.6% | 46.8% | 43.6% |
| Coconut oil* | 20% | 19.5% | — |
| Fish oil* | 0.9% | 2.3% | 2% |
| LC-PUFA-containing oil, (e.g., *Mortierella Alpina* oil)* | 0.5% | — | 1.1% |

*% of weight of total lipid

TABLE 2

The fatty acid composition (PA, MA and SA) of Blends 1-3. The fatty acid composition and the sum of sn-1(3) SFA in each blend was calculated based on the mean composition of in 1 to 21 samples of fat from different world locations

| Name | Blend 1 Amount % of total fat | Blend 1 Amount % total fatty acids | Blend 2 Amount % of total fat | Blend 2 Amount % total fatty acids | Blend 3 Amount % of total fat | Blend 3 Amount % total fatty acids |
|---|---|---|---|---|---|---|
| Myristic acid | 3.4 | 3.6 | 3.3 | 3.5 | 2.7 | 2.9 |
| Palmitic acid | 5.3 | 5.6 | 5.4 | 5.7 | 10.4 | 11.1 |
| Stearic acid | 2.6 | 2.7 | 2.6 | 2.7 | 4.3 | 4.6 |
| Sum sn-1(3) SFA (% of triacylglycerols) | 9.00 | | 8.9 | | 11.2 | |

Example 3

Infant formula compositions

| Nutrient | Invention 1 per 100 kcal |
|---|---|
| Energy (kcal) | 100 |
| Protein (g) | 1.8-2.1 |
| Lactose (g) | 9.0-14.0 |
| Fat blend in Example 1(g) | 4.4-6.0 |
| Sodium (mg) | 20.0-60.0 |
| Potassium (mg) | 60.0-160.0 |

-continued

Infant formula compositions

| Nutrient | Invention 1 per 100 kcal |
|---|---|
| Chloride (mg) | 50.0-160.0 |
| Phosphorus (mg) | 25.0-100.0 |
| Calcium (mg) | 50.0-140.0 |
| Magnesium (mg) | 5.0-15.0 |
| Iron (mg) | 0.4-8.0 |
| Copper (mg) | 0.03-0.12 |
| Zinc (mg) | 0.5-1.5 |
| Iodine (μg) | 10.0-50.0 |
| Manganese (μg) | 1.0-100.0 |
| Selenium (μg) | 1.0-9.0 |
| Fluoride (μg) | 0-100.0 |

Example 4

Materials and Methods:

The in vitro lipolysis model used is designed to mimic the biochemistry of healthy term infants. Briefly, the in vitro model consisted of a two-step lipolysis with a gastric and intestinal digestion. In the gastric step, infant formula were digested in a medium containing NaCl, Tris, maleic acid and egg phospholipids at pH 5.5 during 15 min at 37° C. Then, rabbit gastric lipase (18 U/mL), pepsin (450 U/mL) were added to the gastric medium and incubated for 60 min at 37° C. Prior to the intestinal digestion step, the pH of the gastric digesta was raised to pH 6.5 and then the intestinal medium containing bile salt mixture (2 mM), egg phospholipids, NaCl, Tris and maleic acid was added and incubated at 37° C. for 15 min. Then, pancreatin (30.9 mg/mL) was added to the intestinal medium and incubated for 90 min at 37° C. To stop the intestinal digestion, the samples were kept in ice for at least 3.0 min to stop the digestion process (enzyme activities). Digesta samples were then centrifuged at 13'500 g for 30 min at 4° C. The creamy phase, the supernatant (aqueous phase) and the pellet were collected and calcium content was determined by flame atomic absorption spectrometry in each phase as well as in the infant formula before digestion. Calcium content in the creamy phase and in the aqueous phase correspond to the soluble calcium while the calcium content in the pellet phase corresponds to the insoluble calcium precipitated as insoluble soaps with fatty acids.

Results:

FIG. 1 presents the repartition of insoluble and soluble calcium in different infant formulas after the two-step lipolysis of infant formulas in conditions mimicking the biochemistry of healthy term infants. The insolubility/solubility of calcium was tested in triplicate for all infant formulas. Insoluble calcium is the calcium measured in the pellet fraction under the form of soaps while the soluble calcium is the calcium measured in both aqueous and creamy fractions after the 2 steps of digestion (gastric and intestinal). Results are expressed in % of total calcium and are means of 3 samples for each infant formula. Recovery of calcium from digested infant formulas is between 99-100%.

Results show that the insolubility/solubility of calcium is different between infant formulas containing different amount of sn-1, 3 LCSFA (which are also reported in Table 3 below). In control infant formula containing 24.7% of sn-1, 3 LCSFA as TAG, 44.3% of calcium was insoluble while 56.6% of the total calcium was in the soluble form after digestion. By contrast, in infant formula according to the invention (containing fat bend 2 as described in Example 2) with an amount of sn-1, 3 LCSFA of ≈9% of TAG, the calcium solubility was highest with only 16% of total calcium content recovered in the pellet (insoluble calcium) when compared with control infant formula (sn-1, 3 LCSFA≈25% TAG) (83% vs 56.6% of total calcium). Similarly, the calcium solubility was highest in an infant formula according to the invention (containing fat bend 3 as described in Example 2) containing ≈11% of sn-1, 3 LCSFA (% TAG) when compared with a control formula (84% vs 56.6% of total calcium). Only 16.5% of the total calcium was recovered in the pellet

TABLE 3

| Name | Control formula Amount | | Blend 2 Amount | | Blend 3 Amount | |
|---|---|---|---|---|---|---|
| | % of total fat | % total fatty acids | % of total fat | % total fatty acids | % of total fat | % total fatty acids |
| Myristic acid | 3.8 | 4 | 3.3 | 3.5 | 2.7 | 2.9 |
| Palmitic acid | 20.8 | 21.9 | 5.4 | 5.7 | 10.4 | 11.1 |
| Stearic acid | 3.2 | 3.4 | 2.6 | 2.7 | 4.3 | 4.6 |
| Sum sn-1(3) SFA (% of triacylglycerols) | 24.7 | | 8.9 | | 11.2 | |

Together our results show that the solubility of calcium is the highest in infant formula containing low amount of sn-1, 3 LCSFA when compared to control infant formula. Our solubility results are in good agreement with our concept.

The invention claimed is:

1. A method for at least one of (i) reducing digestive discomfort, (ii) reducing abdominal pain, (iii) reducing an incidence and/or severity of colic, or (iv) reducing an incidence and/or severity of constipation, in an infant or young child in need thereof, the method comprising:
   administering to the infant or young child a composition comprising protein, carbohydrates and lipids,
   the lipids comprising fatty acid (FA) triacylglycerols (TAG), the fatty acid TAG comprising stearic, palmitic and myristic esters,
   wherein the sum of the amount of the stearic, palmitic and myristic esters at the sn-1(3) position of the TAG is less than 13.0% (w/w) of TAG, and the myristic acid represents up to 3.6% of the total FA, the palmitic acid represents up to 11.1% of the total FA, and the stearic acid represents up to 4.6% of the total FA (w/w),
   the lipids comprise a mixture of oils, the mixture of oils is selected from the group consisting of:
   a) 17.3 to 21.1% of rapeseed oil, 11.5 to 14.1% of sunflower oil, 41.9 to 51.3% of high oleic sunflower oil, and 18.0 to 22.0% of coconut oil;
   b) 16.9 to 20.7% of rapeseed oil, 11.3 to 13.9% of sunflower oil, 42.1 to 51.5% of high oleic sunflower oil, and 17.5 to 21.5% of coconut oil; and
   c) 23.9 to 29.3% of milk fat, 15.8 to 19.4% of rapeseed oil, 8.2 to 10.0% of sunflower oil, and 39.2 to 48.0% of high oleic sunflower oil.

2. The method of claim 1 wherein the composition is administered in an amount effective for reducing stool hardness in the infant or young child.

3. The method of claim 1 wherein the composition is administered in an amount effective for increasing bone mineralization, increasing bone strength, and/or increasing bone mineral density in the infant or young child.

4. The method of claim 1, wherein the carbohydrates comprise 99% to 100% of lactose.

5. The method of claim 1, wherein the amount of the protein in the composition is up to 2.1 g protein/100 kcal of composition.

6. The method of claim 1, wherein the protein is a mixture of whey protein and casein having a ratio of the whey protein to the casein between 50:50 and 80:20.

7. The method of claim 1, wherein the protein is partially hydrolyzed.

8. The method of claim 1, wherein the composition further comprises at least one additional component selected from the group consisting of a prebiotic and a probiotic.

9. The method of claim 1, wherein the lipids are selected from the group consisting of docosahexaenoic acid (DHA), arachidonic acid (ARA), eicosapentaenoic acid (EPA and mixtures thereof.

* * * * *